(12) United States Patent
Zavalloni

(10) Patent No.: US 12,728,044 B2
(45) **Date of Patent: *Sep. 8, 2026**

(54) APPARATUS ON BOARD MACHINE FOR PRODUCING FOLDED UNDERWEAR PADS

(71) Applicant: GDM S.p.A., Bologna (IT)

(72) Inventor: Alessandro Zavalloni, Bologna (IT)

( * ) Notice: Subject to any disclaimer, the term of this patent is extended or adjusted under 35 U.S.C. 154(b) by 0 days.

This patent is subject to a terminal disclaimer.

(21) Appl. No.: 19/206,123

(22) Filed: May 13, 2025

(65) Prior Publication Data

US 2025/0352401 A1 Nov. 20, 2025

(30) Foreign Application Priority Data

May 15, 2024 (IT) ........................ 102024000010972

(51) Int. Cl.
*A61F 13/15* (2006.01)
*A61F 13/496* (2006.01)
*B65B 63/04* (2006.01)

(52) U.S. Cl.
CPC ...... *A61F 13/15747* (2013.01); *A61F 13/496* (2013.01); *B65B 63/04* (2013.01)

(58) Field of Classification Search
CPC .......... A61F 13/15747; A61F 13/15577; A61F 13/496; B65H 2801/57; B31B 50/585
USPC .......................................................... 493/418
See application file for complete search history.

(56) References Cited

U.S. PATENT DOCUMENTS 3,376,692 A * 4/1968 Berney .................... B65B 43/39 53/385.1
3,994,486 A * 11/1976 Nystrand ............. B65H 45/161 493/449
5,300,007 A * 4/1994 Kober ...................... D06F 89/00 493/450
6,250,357 B1 * 6/2001 Niedermeyer .... A61F 13/15593 156/227
6,776,316 B2 * 8/2004 Van Eperen ...... A61F 13/15764 223/37
7,399,266 B2 7/2008 Aiolfi
7,500,941 B2 * 3/2009 Coe ................... A61F 13/15747 493/438
2003/0119641 A1 * 6/2003 Reising ............. A61F 13/15756 493/394
2003/0221767 A1 * 12/2003 Vogt .................. A61F 13/15747 156/229
2006/0276320 A1 * 12/2006 Aiolfi .................... B65B 63/045 493/441
2008/0156417 A1 * 7/2008 Schmitz ............ A61F 13/15804 162/122
2008/0311338 A1 * 12/2008 Petersen ........... A61F 13/49014 156/227
2011/0155304 A1 6/2011 Sakaguchi
2011/0247747 A1 * 10/2011 Schneider ......... A61F 13/15747 156/216

(Continued)

OTHER PUBLICATIONS

Italian Patent and Trademark Office, Search Report, Oct. 21, 2024.

*Primary Examiner* — Joshua G Kotis
(74) *Attorney, Agent, or Firm* — Themis Law

(57) ABSTRACT

A method for folding pads shaped as pants includes overturning a first wing and a second wing provided with a hook and loop connection by 180° on a plane of the pad and maintaining the first wing and the second wing in that position until the pad shaped as pants is closed.

16 Claims, 3 Drawing Sheets

(56) References Cited

U.S. PATENT DOCUMENTS

| | | | | |
|---|---|---|---|---|
| 2011/0287919 | A1* | 11/2011 | Umebayashi | A61F 13/15747 493/416 |
| 2012/0152436 | A1* | 6/2012 | Schneider | A61F 13/15747 156/66 |
| 2012/0152695 | A1* | 6/2012 | Coenen | B65H 45/16 198/780 |
| 2012/0190523 | A1* | 7/2012 | Pastrello | B65H 39/14 198/478.1 |
| 2013/0072887 | A1* | 3/2013 | LaVon | A61F 13/15772 604/386 |
| 2013/0130879 | A1* | 5/2013 | Schoon | A61F 13/15747 493/405 |
| 2016/0220422 | A1* | 8/2016 | Schneider | B65H 35/08 |
| 2017/0246046 | A1* | 8/2017 | Paveletzke | A61F 13/49 |
| 2019/0070846 | A1* | 3/2019 | Reinsch | B65H 29/243 |
| 2023/0201047 | A1 | 6/2023 | Piantoni | |

* cited by examiner

APPARATUS ON BOARD MACHINE FOR PRODUCING FOLDED UNDERWEAR PADS

FIELD OF THE INVENTION

The present invention concerns the technical field related to the production of pads.

In particular, the invention concerns an innovative apparatus, and related machine, which allows the pad to be folded in such a way that the pad is packaged once it has assumed the shape of pants.

BACKGROUND OF THE INVENTION

The production of pads has been known for a long time. The pad, as known, serves for the absorption of liquids and is used in both children and adults when the adults suffer from incontinence or similar problems.

The production of pads has been well known for some time and, in this regard, production lines are used, in which a continuous web of product intended to form the pads is made to move forward along a processing path defined by rotatable rollers (or wheels as the case may be), in such a way that during the forward motion the web already processed to form the pad (therefore comprising the various layers of material that make it up) is cut and then folded into a U shape (therefore folded wrapped over) for packaging.

For example, previous publications are known in this regard, including for example publication BO2005A000360 of May 25, 2005, corresponding to U.S. Pat. No. 7,399,266.

In accordance with this publication, the continuous web is made to move forward along a processing path comprising three mutually counter-rotating rollers. In the production process, the continuous web is cut transversely in such a way as to define the single pad which, then, with the aid of the additional two rollers and through the aid of suction systems together with appropriate folding fingers, is folded into a V to obtain a finished product ready for packaging.

Another publication describes a system similar to the previous one, in which, however, there is an oscillating transfer member which is used to facilitate the transfer from one roller to another in the path of processing and folding the product.

The pads thus folded, however, do not maintain their folded condition, i.e. when they are removed from the package they can reopen into a flat form. In particular, they are simply folded in two halves one on top of the other but they are not stably closed to form pants.

The pads commonly produced have side wings so that they can instead be closed with the shape of pants, maintaining this shape of pants. In particular, a first wing emerges from one flank while a second wing emerges from the opposite flank at one longitudinal end of the pad. The first wing is connected with a third wing in line with it and arranged at the opposite longitudinal end and, in the same way, a fourth wing is in line with the second wing at the opposite longitudinal end.

A process is known that allows those pads to be packaged with the wings already connected to each other and therefore with this shape of pants so as to be ready for use and to be easily worn.

The possibility of production and consequent packaging already with this shape of pants, possibly adjustable through again said wings, is therefore known.

More particularly, such wings (therefore said first wing, second wing, third wing and fourth wing) can be equipped with a quick connection system, for example with a hook and loop connection system (commonly called Velcro® in the trade), in which the fibers of the Velcro® material (generally the fibers relating to the material of which a wing is made) are hooked to the layer having the hooks, with a therefore stable and easily removable connection that allows a quick closure and a quick release.

Then, for example, the first wing and the second wing can provide for the hook system to connect with the fibers relative to the material for making the third wing and the fourth wing.

A technical problem is being able to hook together, already in the production step before packaging, these wings provided with a connection system (for example with Velcro®) in order to give the pad the shape of pants and therefore to be able to package it already with that shape of pants.

To perform this operation it is necessary to overturn a pair of wings, i.e. for example the first wing 101 and the second wing 101, on the plane 100 of the pad to bring their connection means, for example the hooks of the Velcro®, to be connected with the complementary connection means (for example said fibers) present in the other pair of wings, i.e. for example the third wing and the fourth wing.

This overturning is necessary because the connection of the wings, in the pants-like closure, must form a flat strip that surrounds the flank, making sure that the face of the wing in contact with the skin is the one without connection means, in particular without the hooks, for obvious reasons of comfort.

More particularly, therefore, with reference to FIG. 1, the stretched pad 100 shows the surface 100 intended to come into contact with the body of the user together with the faces of the first wing (101), second wing (101), third wing (102) and fourth wing (102) that also come into contact with the body.

If, for example, the Velcro® system is used, the hooks of the Velcro® must be positioned on the face of the wing opposite the plane 100 of the pad (see FIG. 1), in such a way that the connection requires overturning the wing 101 (see FIG. 2) and thus ensuring that the wing face that comes into contact with the body during use is the smooth part.

The currently known solutions through which this overturning is carried out are not reliable as the wings, along the processing path, are only partially folded and, following this partial folding, are maintained free and can flutter so that the coupling between them to carry out the closure is not precise. It is clear that in accordance with this solution the process is not reliable and it is therefore not certain that the correct hooking of a wing can take place in order to couple it with the complementary one, especially when the production speeds are very high and therefore the product travels at high speeds, thereby increasing the free fluttering of the wings. The faster the product is moved forward, the easier it is for the wings to flutter uncontrollably, preventing intended systems from being able to couple the wings correctly and to perform this operation in a precise and reliable manner.

There is therefore a problem of reliability in the production process of shaping the pad like pants.

SUMMARY OF THE INVENTION

Therefore, it is an object of the present invention to provide an apparatus that solves at least in part the aforementioned technical drawbacks.

In particular, it is the object of the present invention to provide an apparatus that, in the production of pads, allows folding and coupling together the wings with which the pad is provided, in order to close the pad with the shape of pants, so as to provide a process that is reliable and precise, even at high production speeds.

These and other objects are obtained with the apparatus for folding a semifinished product of an absorbent product for sanitary use to form a product with the shape of pants, as described hereinafter.

This apparatus comprises:

A path of forward motion for said semifinished product;

Said path of forward motion comprising transversal folding means configured to fold said semifinished product transversally with respect to the path of forward motion in such a way as to fold it into two parts overlapping each other to form said product with the shape of pants.

In this way, advantageously, the semifinished product is folded, in use, into two parts overlapping each other, thus forming the finished product, i.e. said pants.

In accordance with the invention, upstream of said transversal folding means there are provided folding means of the wings.

In order to obtain the final product with the shape of pants, it is necessary that the wings with which the semifinished product is provided couple with each other. Said wings, in fact, as already introduced in the known art, comprise the connection means that allow a coupling between them of the releasable type, for example with Velcro®.

Said folding means of the wings are therefore configured to overturn and maintain laid in a laid position on a surface of said semifinished product a first wing emerging from a flank of the semifinished product and a second wing opposite the first wing and emerging from the opposite flank of the semifinished product until completion of formation of said product with the shape of pants.

In this way, advantageously, both the first wing and the second wing are maintained in the overturned position on the surface of the semifinished product, thus exposing upwards the first connection means with which they are provided so that they are ready to engage in a releasable manner, following wraparound folding of the semifinished product, with the complementary second connection means with which the third wing and the fourth wing are provided that are present at the opposite end of the semifinished product.

In this way, the semifinished product is permanently closed in a configuration with the shape of pants.

Thanks to this solution, all the aforementioned technical drawbacks are solved.

In particular, the wings, in particular the first wing and the second wing, are maintained stably in an engagement position ready to be able to connect precisely and stably respectively with the third wing and the fourth wing.

Unlike prior art solutions, maintaining at least one pair of wings in a stable position on the surface of the semifinished product allows a subsequent precise coupling even at high production speeds.

The term "upstream" and "downstream" are understood in the well-known classical sense in which, moving along the processing direction in the processing path, from a point of origin called "upstream" it is moved to a subsequent point along the processing direction called "downstream".

In particular, therefore, "upstream" of said transversal folding means therefore means that, moving according to the direction of forward motion of the product being processed along its processing path, the folding means of the wings are intercepted first and only subsequently (therefore moving downstream) the transversal folding means follow.

Advantageously, said folding means of the wings are configured to fold said first wing and second wing by 180° or approximately 180° and keep them in said folded position.

In this way, as mentioned, said wings can be overturned on the surface of the semifinished product, keeping them stably in position in order to guarantee a precise coupling between the wings.

Advantageously, in accordance with a possible preferred configuration of the invention, said folding means of the wings are integrated on board said path of forward motion.

In this way, therefore, the set of the components that generate said path of forward motion is further equipped with such folding means of the wings.

For example, advantageously, said path of forward motion may comprise or may be formed or consist of at least one rotatable wheel.

According to a preferred form of invention, said path of forward motion may comprise or may be formed or may consist of at least three mutually rotatable wheels arranged to form said path of forward motion.

In accordance with this solution, therefore, the three wheels are arranged in such a way as to cause the forward motion of the semifinished product and with an arrangement and direction of rotation such that the product moves forward and at the same time is folded into two halves to form the product with the shape of pants.

Said folding means of the wings are therefore suitably arranged on at least one of said at least one wheel or in any case on one wheel in the case of at least three wheels and keep the wings folded until completion of the product with the shape of pants.

Advantageously, in all the aforementioned cases, said folding means of the wings comprise at least one airflow.

Advantageously, this airflow is integrated on board said path of forward motion and is adapted to fold a wing of said semifinished product lifting it with respect to the surface of the semifinished product by an angle of 90° or approximately 90°.

In this way, advantageously, the wing that extends radially from the body of the semifinished product is lifted into a position to form a right angle.

According to an advantageous form of invention, at least two side shoes connected to the edges of said path of forward motion can be comprised.

For example, one shoe can be placed on a flank of said path of forward motion and the other shoe can be placed on the opposite flank of said path of forward motion in such a way as to intercept said first wing and second wing.

Advantageously, therefore, said at least two side shoes are provided with one or more holes for the passage of said airflow.

In this way, advantageously, the air jet that lifts the wing to approximately 90° is correctly directed through the shoe provided with a hole.

As mentioned, said path of forward motion is formed by at least one rotatable wheel and preferably by at least two or even more preferably by at least three rotatable wheels.

In all of the above cases, said shoes are on board at least one wheel.

Advantageously, according to a possible preferred form of invention, said shoes can have a flat geometry which traces a segment of chord of said wheel where they are arranged.

In a possible alternative, said shoes may have a circular geometry in such a way as to follow the arc of circumference of the wheel.

The person skilled in the art will therefore be able to evaluate the alternative solution that he deems most suitable for his purposes.

According to an advantageous form of invention, said folding means of the wings comprise, in combination with said airflow, overturning and maintaining devices integrated on board said path of forward motion and configured to complete overturn of the wing laying said wing on the surface of the semifinished product and maintaining it in said laid position.

In this way, therefore, the airflow, for example through the shoe, brings the wing into a position at right angle or in any case lifted with respect to the path of forward motion or with respect to the surface of the semifinished product and, subsequently, said overturning and holding devices complete the overturn on the plane of the semifinished product constituted by said surface.

According to a possible solution, said overturning and maintaining devices can for example comprise one or more fingers configured to perform overturn at least on the surface of the semifinished product and connected to said path of forward motion. In this sense, said fingers move integrally with the motion of the path of forward motion (for example, with the rotation of the wheel).

According to a preferred configuration of the invention, said fingers can for example be further movable to intercept the wings to be folded.

In particular, the Applicant has experimentally verified the achievement of excellent performance in the event that these fingers are configured to perform axial pushing movements such as to intercept the product arranged in the path of forward motion.

In this way, in use, said fingers intercept the product and they act on the wing to overturn it from the lifted position at 90° to the position laid on the surface, thus completing a rotation of 180° of the wing.

In a possible solution, advantageously, the movement of said fingers can for example occur by means of a cam system.

Advantageously, said path of forward motion can therefore comprise one or more areas provided with suction to maintain the wings in said overturned position on the surface at least until end of activation of the transversal folding means to complete the product with the shape of pants.

In essence, therefore, the wings, once they are overturned, can be kept in a position laid on the surface for example by suction until completion of the final product.

As an alternative to suction, or in combination with such suction, said fingers remain in the position intercepting said path of forward motion for maintaining said wings in said overturned position on the surface at least until end of activation of the transversal folding means.

In this way, the fingers facilitate maintaining the overturned position by acting in combination with suction or, alternatively, the suction may not be present with the fingers that operate this maintenance in the overturned position.

In all the aforementioned cases, advantageously, said fingers have a shape, in particular preferably the thickness, such as not to fully cover said wings on which they act in use.

In this way, advantageously, said fingers do not interfere with the connection area of the wings.

In particular, said fingers do not interfere with the coupling means responsible for the releasable coupling of the wings.

In particular, they do not interfere with the first coupling means with which said first wing and second wing are provided and which couple with the complementary second coupling means with which the third wing and the fourth wing are provided.

In a possible variant, without prejudice to what is described above, the airflow that is responsible for the first folding at 90° of the wings may possibly be outside the path of forward motion and not be integral to it.

According to a preferred solution, narrowing means may be comprised and arranged on the opposite side of the folding means of the wings with respect to the longitudinal length of the semifinished product.

These narrowing means are configured to narrow, in use, the portion of semifinished product longitudinally opposite to said first wing and second wing.

In this way, advantageously, the wings that must be coupled together are placed perfectly in line or in the coupling axis.

According to a possible solution, said narrowing means can for example comprise at least one shiftable suction, for example through shiftable shoes.

In this way it is possible to drag, in use, the portion of the semifinished product causing a transversal narrowing thereof.

Notwithstanding the foregoing, according to a further alternative form of invention, said folding means of the wings instead of being fully integrated on board the path of forward motion (and therefore moving integrally with it as they are integral therewith) can be partly integrated on board said path of forward motion and partly be outside said path of forward motion.

In this case, said folding means of the wings may comprise at least one airflow integrated on board said path of forward motion and adapted to fold a wing of said semifinished product lifting it with respect to the surface of the semifinished product by an angle of 90° or approximately 90°.

As mentioned, also in this case advantageously at least two side shoes can be comprised and connected to the edges of said path of forward motion.

In particular, advantageously, one shoe can be placed on one flank of said path of forward motion and the other shoe can be placed on the opposite flank of said path of forward motion in such a way as to intercept said first and second wings, the two side shoes being equipped with holes for the passage of the airflow.

Advantageously, what has already been said above applies, i.e. said shoes have a flat geometry which traces a segment of chord of said wheel where they are provided or, alternatively, said shoes have a circular geometry in such a way as to follow the arc of circumference of the wheel.

In all the configurations described, it is reminded here that the path of forward motion is movable so that the product being processed is dragged, for example in the case of rotatable wheels.

In accordance with this solution, said folding means of the wings comprise, in combination with said airflow, overturning and maintaining devices which, however, are now external to said path of forward motion.

Advantageously, said folding means of the wings are configured to complete overturn of the wing laying said wing on the surface of the semifinished product and maintaining it in said laid position.

Advantageously, said overturning and maintaining devices comprise one or more fingers configured to perform overturn at least on the surface of the semifinished product.

However, they are now arranged externally to said path of forward motion.

Also in this case, advantageously, said fingers can be movable in the transversal direction with respect to the path of forward motion.

These fingers can therefore be configured to perform axial pushing movements such as to intercept the path of forward motion so that, in use, by acting on the wing to overturn it from the lifted position at 90° to the position laid on the surface thus completing a rotation of 180° of the wing.

Also in this case, advantageously, as mentioned, the movement of said fingers can for example occur by means of a cam system.

Advantageously, in this case, said path of forward motion may comprise one or more areas provided with suction to maintain the wings in said overturned position on the surface at least until end of activation of the transversal folding means.

A solution is not excluded in which even the airflows responsible for the first fold at 90° of the first and second wing can be off board, actually having a solution with said folding means of the wings fully off board.

In all the aforementioned cases, advantageously, narrowing means can be comprised and arranged on the opposite side of said folding means of the wings with respect to the longitudinal length of the semifinished product and configured to narrow, in use, the portion of semifinished product longitudinally opposite to said first wing and second wing.

In this case, advantageously, said narrowing means can be arranged on board said path of forward motion.

Advantageously, said narrowing means can comprise also in this case at least one pair of shoes.

For example, one shoe can be arranged on one flank of said path of forward motion and the other shoe can be arranged on the opposite flank.

The shoes therefore have holes for the passage of a suction.

Advantageously, therefore, said shoes are movable in a transversal direction in such a way as to narrow said portion of the semifinished product.

Advantageously, said pair of shoes can be movable, for example through a cam system.

Advantageously, for example, said path of forward motion provided with said pair of shoes can comprise, in an area adjacent to said pair of shoes, a free area and/or a cavity adapted, in use, to house the excess material of the semifinished product in the narrowing step.

In this way, the excess material is properly collected.

Advantageously, as already mentioned, said path of forward motion can be formed by at least one wheel or preferably by at least three wheels.

Said pair of shoes can be on board at least one wheel.

Advantageously, in all the configurations described, the path of forward motion is formed by at least two rotatable wheels, preferably at least three rotatable wheels and whose rotation therefore determines a motion of the path of forward motion and a consequent dragging of the product being processed.

Said narrowing means are in the form of a suction for making the semifinished product adhere to the surface of the path of forward motion defined by said at least three wheels.

In combination with the suction there is a surface geometry having a buckling present in at least one of said three wheels such as to keep the product in adhesion thus causing a narrowing of the semifinished product that extends into the buckling.

Advantageously, in a possible solution, the path of forward motion is formed by at least three wheels and wherein the first wheel has a cavity in its central area to accommodate the semifinished product and raised side areas.

In this way, the second wheel that is coupled in a counterrotating way with the first wheel has a complementary shape so that it has a raised central area and two side areas with a cavity.

Advantageously, therefore, the third wheel reproduces the configuration of the first wheel.

Advantageously, moreover, in all the configurations described, lateral compression wheels 51 for pressing the semifinished product when it has been closed to form a product with the shape of pants through said transversal folding means can also be comprised.

This ensures a secure coupling of the wings.

An object of the present invention is also a production line for absorbent products for sanitary use comprising an apparatus according to one or more of the above characteristics.

BRIEF DESCRIPTION OF THE DRAWINGS

Further features and advantages of the present apparatus and relative production line, according to the invention, will become clearer with the following description of some of its embodiments, made by way of non-limiting example, with reference to the accompanying drawings, in which:

FIG. 1 shows the first wing 101 and the second wing 101 that branch from the flank of the pad and with such first wing and second wing provided with a first Velcro® system part in a way such as to be able to couple, each one, with the relative third wing 102 and fourth wing 102 that comprises the second Velcro® part; FIG. 2 shows said first wing 101 and second wing 101 folded on the plane 100 of the pad in order to bring the first Velcro® system part facing in such a way as to connect with the second Velcro® system part present on the third wing 102 and fourth wing 102;

DETAILED DESCRIPTION OF EMBODIMENTS OF THE INVENTION

The present invention is now described in detail with reference to the accompanying figures.

Figure 1:
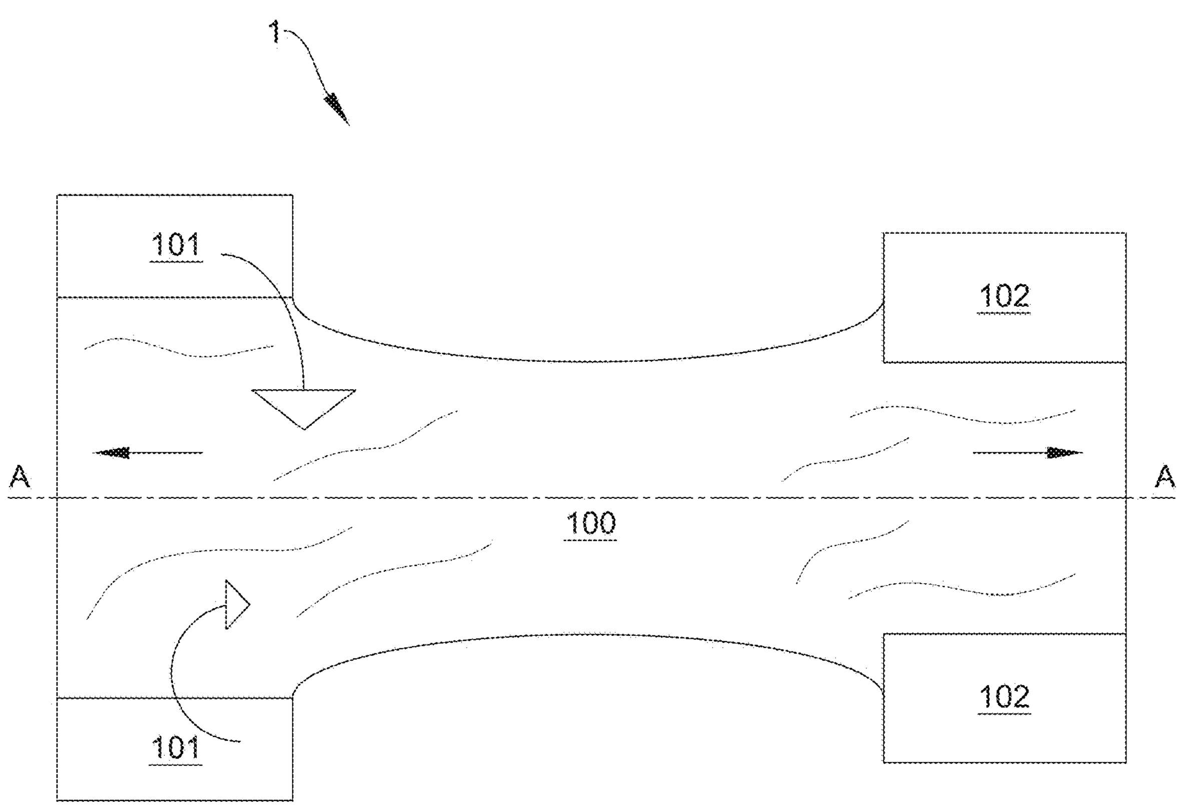
FIGS. 1 and 2 show a pad according to the known art in a stretched (or open, as the case may be) position; in particular.

FIG. 1 shows a schematization of the semifinished product 1 (i.e. the pad 1 before it is closed to form the pants 2, i.e. the finished product to be packaged) well known in the state of the art as already described in the prior art.

Figure 2:
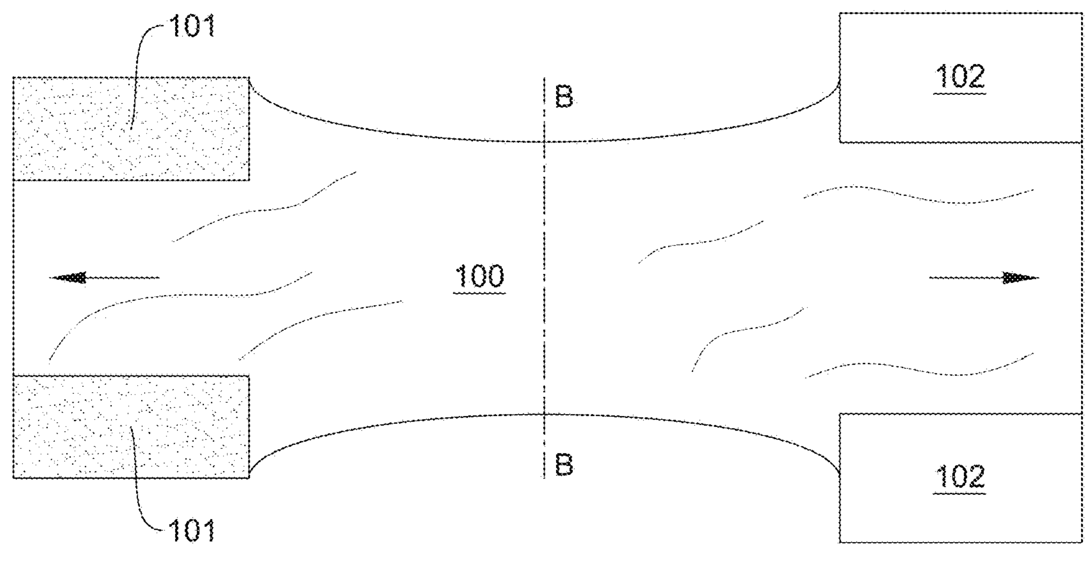
Figures 3, 4, 4A, 5, 5A, 7:
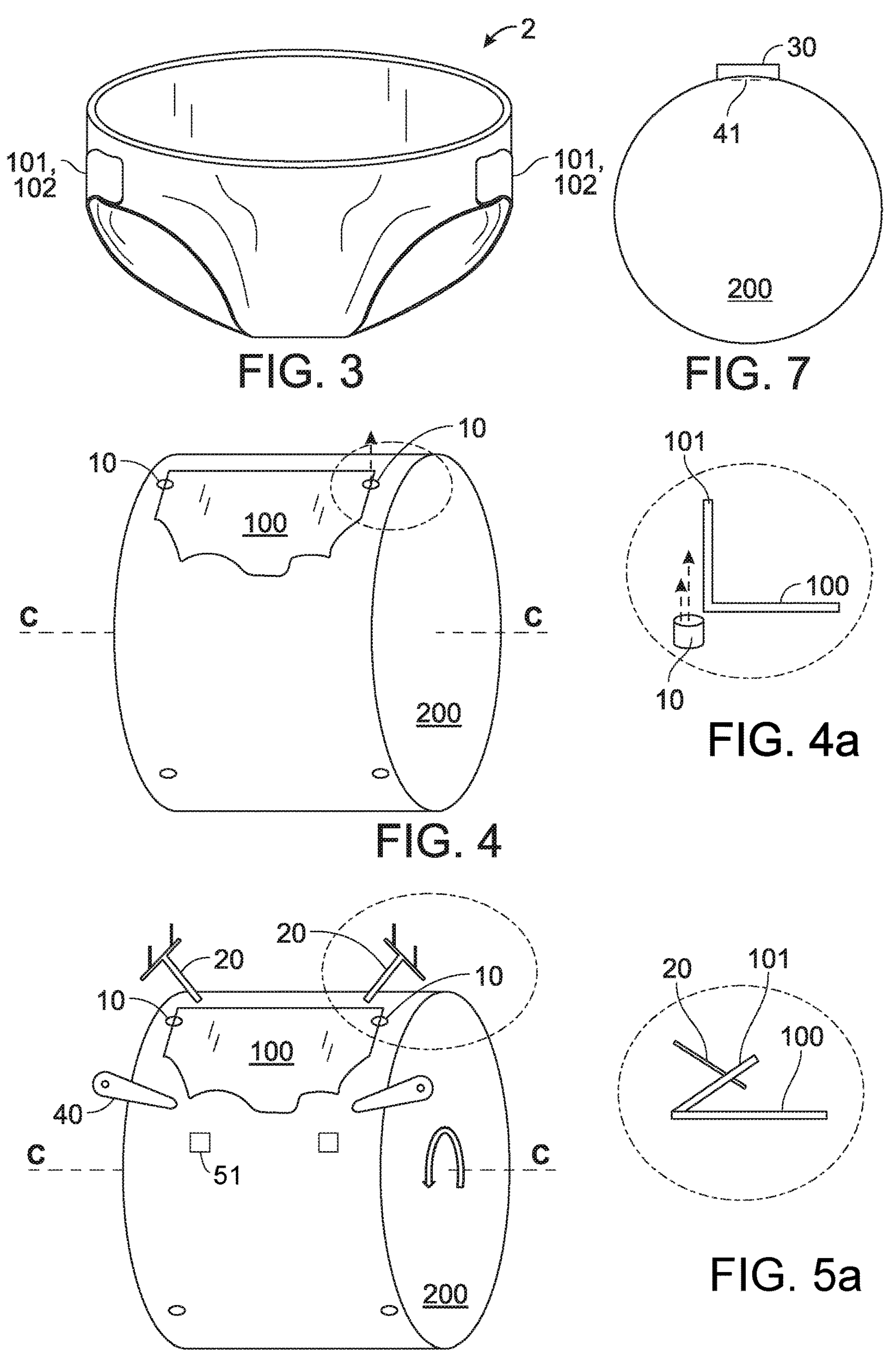
FIG. 3 shows the pad closed with the shape of pants 2 through the Velcro® system.
FIGS. 4 and **4*a* show a schematization of the roller 200 on which the pad passes in its processing and folding process and the figure highlights the nozzle 10 which, with an air jet, brings the first wing and the second wing 101** to rise with respect to the plane of the pad.
FIGS. 5 and **5*a* show a possible solution in which special folding devices 20, for example in the form of fixed fingers 20, are arranged to intercept the path of forward motion of said first wing 101 and second wing 101 when lifted at right angles, in order to complete their folding by completing to overturn them and therefore laying them on the plane 100** of the pad, thus completing a rotation at about 180°.
FIG. 7 shows that shoes 30 may be arranged on the roller 200 to trace a segment of chord of the roller 200.

It develops along a longitudinal line A-A and can be folded along the transverse line B-B (see FIG. 2) to form the pants 2 schematized in FIG. 3.

The semifinished product 1 comprises the wings (101, 102) which thus extend radially to the outside of the body.

In particular, a first wing 101 and a second wing 101 are provided which extend from the two flanks of the pad 1 and which are intended to engage with further a third wing 102 and a fourth wing 102 that extend in the same way from the two flanks of the pad. Therefore, with respect to the transverse line B-B of FIG. 2, said first wing 101 and second wing 101 extend from one part of the pad while the other two complementary wings 102, i.e. the third wing 102 and the fourth wing 102, extend from the opposite part of the line B-B.

As mentioned above, the reciprocal connection of a wing 101 with the complementary wing 102 occurs through connection means (generally of a quick type) which provide first connection means adapted to releasably engage with the second complementary connection means (generally of a quick type as mentioned).

In particular, the first wing and the second wing may comprise the first connection means (for example of a quick type) and the third and fourth wing may comprise the complementary second connection means (for example of a quick type) or vice versa.

The pad in top view of FIG. 1 is arranged along a processing line and in a stretched position.

The surface (or plane, as the case may be) 100 shown is the one intended to come into contact with the body of the subject wearing it. FIG. 3 shows when the pad is closed to form the pants 2.

As shown in FIG. 1, the two wings 101 (first wing and second wing) are therefore provided along the longitudinal length of the stretched pad. One of these emerges from one flank and the other, opposed, emerges from the opposite flank. On the opposite part along the longitudinal direction there are the other two complementary wings 102 (i.e. the third wing 102 and the fourth wing 102) always arranged on the two flanks in such a way that the third wing 102 can be coupled with the first wing 101 facing on the same part thereof and the fourth wing 102 can be coupled with the second wing 101 for performing pants-like closure as per FIG. 3.

To perform this operation, as shown in FIG. 1 and as anticipated in the prior art, it is necessary to overturn said first and second wing 101 on the plane 100 of the pad.

This is necessary because the connection of the wings 101-102, in the pants-like closure, must form a flat strip that surrounds the flank, making sure that the face of the wing in contact with the skin is the one without connection means for obvious reasons of comfort.

For this reason, the part of the connection systems arranged in the wings 101 (first wing and second wing), for example the hooks of a Velcro® (if Velcro® is used), are arranged on the face of the wing 101 opposite to the face that is visible in FIG. 1 (i.e. the face intended for contact with the body). In other words, the hooks of the Velcro® are arranged on two opposed wings (for example the first wing 101 and the second wing 101) on the face of both such wings 101 which is opposite the surface 100 of the pad intended to come into contact with the body of the user.

It is therefore necessary, as shown in FIG. 2, to have to overturn said first wing 101 and second wing 101 thus making visible the quick connection systems as per FIG. 2 (for example the hooks of the Velcro® as mentioned) which are arranged on said wings 101 and which serve to connect with the fibers of the further third wing and fourth wing 102.

Said third wing and fourth wing 102 must not be overturned as the fibrous material that is coupled with the hooks (in the case of use of Velcro®) must be present on the face of the wing 102 facing the outside of the surface 100 (see always FIGS. 1 and 2). This fibrous material can be applied with a special layer or be part of the material itself constituting the wing 102. Upon coupling, the resulting strip in contact with the body is substantially the only face of the wing 101 without the quick connection means.

In a preferred form of invention, said connection means (and therefore the first connection means and the complementary second connection means) may provide for the use of Velcro®, whereby having quick-type connection means.

The Velcro® system is itself well known and provides for a series of hooks emerging from one surface that are engaged in a series of fibrous elements emerging from another surface. When they are coupled, the hooks of one surface are engaged with the fibrous elements of the opposed surface.

In the proposed solution, therefore, said first wing and second wing 101 can be provided for example with such hooks of the Velcro® with the surface relative to the third wing 102 and fourth wing provided with a further surface of fibrous material and/or vice versa.

In this sense, therefore, said first wing 101 and second wing 101 can therefore provide first Velcro® quick connection means 101 (for example said hooks or fibrous material) adapted to releasably engage with the second Velcro® complementary quick connection means 102 which are obviously the complementary ones of said first Velcro® quick connection means 101 mentioned.

In a variant of the invention, however, it is not excluded that the wings can provide first quick connection means and second quick connection means complementary to each other different from Velcro®.

As already introduced, in order to have a correct closure of the pad with the shape of pants, it is necessary that the two wings 101 (i.e. the first wing and the second wing) that are at one end of the pad along its longitudinal length (A-A) be overturned on the body of the pad itself according to the arrow direction indicated in FIG. 1. In fact, the first quick connection means present on these two wings 101 are arranged, in FIG. 1, on the face of the wings 101 opposite that visible in FIG. 1. Therefore, for the connection to take place between the first quick connection means and the second quick connection means present on the third wing and fourth wing 102, it is necessary that said first wing 101 and second wing 101 be overturned by 180° on the plane of the pad, exactly as indicated in FIG. 2. FIG. 2 shows in fact with a schematization the visible first quick connection means (for example as said first Velcro® quick connection means). The third wing and fourth wing, on the other hand, must not be overturned and are already ready for connection.

Therefore, as already described, the hooks of the Velcro® can be arranged (for example by gluing a special layer provided with hooks) on the face of the first wing and second wing 101 opposite the one seen in FIG. 1 in such a way that, following overturn said first wing and second wing 101 on the plane 100 of the pad, said first quick connection means (for example the hooks) are visible, i.e. facing upwards (therefore to the outside of the plane 100 of the pad).

The second complementary quick connection means, in this example case therefore the fibrous material, do not need to be applied to the third wing and fourth wing but they can be part of the same third wing and fourth wing if these are made of a material of fibrous nature.

In all the aforementioned cases, when the pad, along its processing path, is folded along the transverse line B-B and further pressed, this involves an engagement of the first connection means (for example of the quick type) with the complementary second connection means (for example of the quick type), ensuring that the surfaces of the first wing and second wing 101 that face the inside of the annular pants, therefore in contact with the skin, are the smooth surfaces without the connection systems.

That said, therefore, the invention now describes in more detail a folding methodology of said first wing and second wing 101 and the relative apparatus that allows such folding.

In this way, therefore, it is possible to fold said first wing and second wing by approximately 180° to bring them in any case to stretch above the plane 100 (or surface as the case may be) of the pad, thus bringing them from the configuration of FIG. 1 to that of FIG. 2.

The motion takes place by means of a first rotation that brings the wing 101 at an angle of about 90° with respect to the plane 100 which is followed by a second rotation that brings the wing to the position laid on the plane 100 whereby completing a rotation of about 180°.

In particular, transversal folding means 40 are comprised along the processing path of the semifinished product, which cause a folding of the semifinished product transversely to obtain the product shaped as pants.

In accordance with the invention, upstream of said transversal folding means, folding means (10, 20) of the wings are provided and configured to overturn and maintain laid in a laid position on a surface (100) of said semifinished product a first wing (101) emerging from a flank of the semifinished product and a second wing (101) opposite the first wing (101) and emerging from the opposite flank of the semifinished product (1) until completion of formation of said product shaped as pants (2).

In essence, as shown in FIG. 1, the first wing 101 and the second wing 101 are overturned (see arrow direction) on the plane 100 of the pad.

This occurs through said folding means of the wings.

One or more airflows are part of these folding means of the wings, which therefore lift the wing (i.e. the first wing and the second wing) bringing it into a configuration at 90° with respect to the plane 100, as for example schematized in FIG. 4.

This therefore represents a first part of this rotation, the rotation then having to be completed by laying the first wing 101 and the second wing on the plane 100 of the pad in such a way that said first wing and second wing are ready to engage with the other third wing 102 and fourth wing 102.

Therefore, along the processing path where the product moves forward, when it is necessary to lift the wing 101 to overturn it on the plane of the pad, this first rotation can take place by means of this airflow.

In particular, the pad travels on a rotatable roller that transports it along the processing path towards the folding section where the folding of the pad takes place along the axis B-B.

FIG. 4 shows a roller of this path in which airflows 10 can be provided arranged based on the width of the product being processed and which projects an air jet upwards. The air jet intercepts the wings 101 of each pad during this production step and maintains said first wing 101 and second wing 101 in a lifted position at 90° (i.e. at right angles or substantially at right angles) with respect to the plane 100 of the pad.

The figure shows in an enlarged view a schematization of the nozzle 10 from which the air jet that lifts the wing 101 is projected.

FIG. 4 in the enlarged portion shows the arrangement that the wing 101 assumes and which, as mentioned, can be at 90° or at about 90° with respect to the plane 100 of the pad.

The nozzles can be obtained in the body of the roller.

A solution of a jet coming from nozzles not integrated into the path of forward motion, therefore external to the roller, is not excluded.

However, preferably, the preferred configuration of the invention provides that at least two side shoes are provided and connected to the edges of said path of forward motion.

The shoes are, in fact, a kind of block, for example, made of metal.

One shoe is placed on one flank of said path of forward motion and the other shoe is placed on the opposite flank of said path of forward motion in such a way as to intercept said first wing and second wing.

These at least two side shoes are therefore equipped with holes for the passage of said airflow.

Continuing in the structural description of the invention, it is then necessary to be able to complete the overturning by bringing the wing 101 to lie on the plane of the pad 100.

For this purpose, therefore, the folding means introduced above (and comprising the airflow (s)) comprise overturning and maintaining devices 20.

These can be on board the path of forward motion or they can be placed outside the path of forward motion.

Solution on Board the Path of Forward Motion:

In a possible solution, fingers 20 can be used that are nothing more than extensions. These can be mounted on board the path of forward motion and can be controlled according to a motion, for example of translation. The motion can take place through actuators or cam systems. In any case, the fingers are integral with the path of forward motion, so they move integrally with it (for example, in the case of rotating rollers, they are mounted on board the roller). They, in addition, move further in order to intercept the wing that is in the position of FIG. 4 (i.e. placed at right angle to the plane 100) to lie it on the plane 100 as per FIG. 5.

The fingers, once they have folded the product on the plane 100, can be pulled back from the position intercepting the first wing and the second wing and, in this case, the wings are kept in said overturned position on the plane 100 through a suction.

Alternatively, these fingers can instead be kept in contact with the first wing and the second wing overturned on the plane 100 precisely to keep these wings in overturned position until formation of the product shaped as pants when the semifinished product is folded transversely.

In this case, of course, the fingers preferably have a shape such as not to interfere with the surface of the first and second wing which comprise the releasable connection mechanism, for example Velcro® as already mentioned.

In this case, therefore, the fingers remain in contact with the wings, moving integrally with the forward motion of the product as they are integral with the path of forward motion.

Solution External to the Path of Forward Motion:

The above also applies in the case of fingers arranged externally to the path of forward motion.

In this case, they do not move integrally with the path of forward motion.

As already mentioned, these fingers can be in the form of extensions in this case, however, they are placed externally to the roller and fixed to an external supporting structure as schematized in FIG. 5.

These fingers (or extensions as the case may be) are arranged in such a way as to project towards the two flanks of the roller according to an inclination such as to intercept said first wing 101 and second wing 101 folded at 90°, thus causing their further rotation on the plane 100 of the pad during the movement of forward motion of the product which is obtained through rotation of the roller which integrally drags the product with it. These fingers are particularly simple as they are fixed, that is, not provided with any motion but they are simply arranged according to a certain inclination and arrangement such as to intercept the path of forward motion of the product, in particular such as to intercept said first wing and second wing during passage thereof, in order to fold said wings 101 on the plane 100 of the pad.

In other words, the completion of the rotation takes place during the forward motion of the product along the processing path by means of rotation of the roller that brings said first wing and second wing to intercept, during the forward motion, said fixed devices which can be, as said, fixed fingers.

FIG. 5 schematizes this simple solution with the fingers, or extensions as the case may be, which are fixed and arranged according to a certain inclination that completes folding of the first wing and second wing, bringing them to lay on the plane 100 of the pad.

In order to maintain this laid position at 180°, since the fingers are fixed and external to the path of forward motion, special air suctions per se already known in the sector can be used to maintain the product adhering to the roller during forward motion.

This suction has already been introduced previously regarding the description of the fingers present in the path of forward motion.

Then, for example, immediately downstream of the fingers that cause said further overturning by further 90° of said wings 101, a special suction can be activated to maintain said first wing 101 and second wing 101 in the folded position of FIG. 2.

The technology is known to provide, in such processing rollers, sectors of suction holes that are activated upon reaching a certain angle of rotation such that the roller can be synchronized with such suction holes such that they are activated whenever the portion of product with the wings 101 reaches and/or passes past said folding fingers 20.

In this way, said first wing 101 and second wing 101 are maintained well folded on the product until the step in which, as already known from the previous documentation, the product is folded into two along the transverse line (B-B) to form the product shaped as pants and therefore with the wings 101 that have been coupled with the complementary wings 102.

Notwithstanding what has been said so far, in a further variant the folding devices 20 can be movable as already described but still external to the path of forward motion.

For example, similar to what is described in FIG. 5, such folding devices 20, for example always in the form of fingers or extensions in general, can be fixed to a structure external to the roller and can be provided with a motion for example of rotation or roto-translation or simple translation that facilitates the operation of intercepting the wing 101 to fold it on the plane 100.

As already described, therefore, there is a special movement mechanism that moves these fingers in order to intercept said first wing and second wing, thus allowing a more precise folding. The motion can for example be simple translation from the outside to the inside towards the roller, hence with said fingers mounted on a translating support structure.

Once the two wings (i.e. the first wing and the second wing) have been folded on the plane 100 of the pad, the fold can be maintained always through suction as already mentioned above.

In an alternative, the fingers that are movable as they are mounted on a movable support for intercepting the fingers can also follow the forward motion of the product such that the mobility is such that it both determines the fold and then maintains it with the fingers that press said first wing and second wing 101 into place as they move forward along the path. In this case, suction would therefore not be necessary.

However, since the fingers in this case are external to the path of forward motion (in other words, they are not integral with the roller), a movement system that moves them in order to follow the forward motion of the product being processed along the path is necessary. As already described above, in accordance with this solution, of course, the thickness and geometry of the fingers 20 in general must be such as not to interfere with the quick connection means with which the wing 101 is provided precisely so as not to prevent the connection step with the complementary wing 102.

Once the coupling between the wings 101 and 102 has taken place, the fingers 20 can be pulled back disengaging and reposition themselves to resume the cycle with the next incoming product.

In a further variant, the mobility of the fingers as mentioned may be such that it determines the 180° folding of the wing 101 without, however, following it in the path of forward motion, thus requiring the action of suction to maintain the wing resting on the product.

Even in this configuration, the airflow that makes the first fold at 90° may possibly be external to the path of forward motion.

In all the aforementioned cases, both in the case of fingers on board the path of forward motion and off board the path of forward motion, an action on the complementary wings 102 (third wing and fourth wing) may also be necessary in order to bring them into a precise position of perfect coupling with said folded first wing and second wing 101 as described above. In this way, when the pad is closed in a wraparound manner along the transverse axis B-B, the coupling is precise with the wings between them in line or in axis, as the case may be.

Narrowing means 30 are therefore provided for this purpose.

Figure 6:
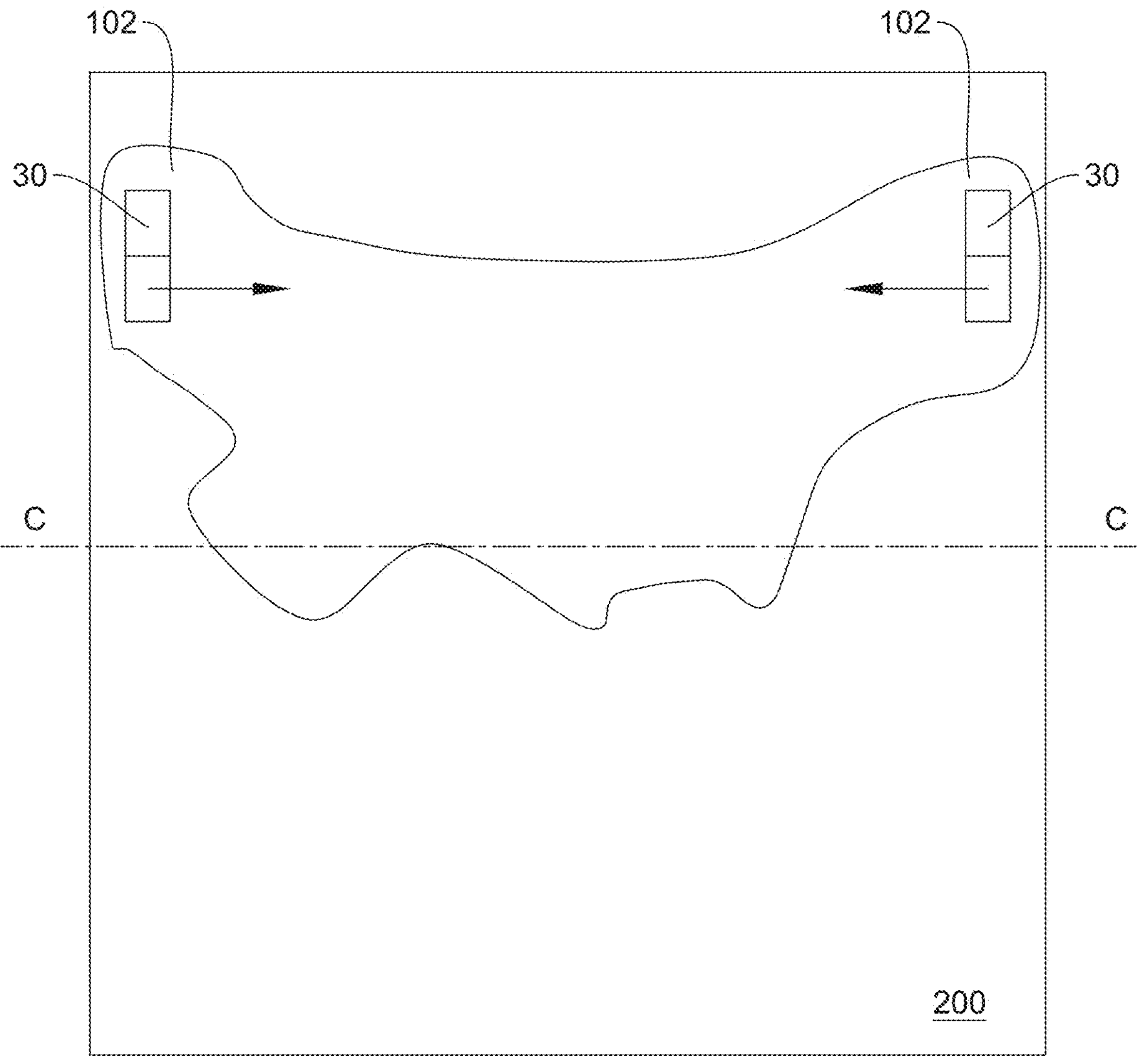
FIG. 6 shows a solution in which two blocks 30 translatable and opposed to each other (said shoes 30 in technical jargon), for example translatable through special guides, integrate in themselves one or more suction nozzles that therefore suck the part of the pad that is positioned above them; specifically, said first wing and second wing are blocked by the nozzles of said shoes; in this way said shoes can be drawn close to each other according to the arrow direction of FIG. 6 so that by making sure that the relative first wing and second wing are drawn close to each other aligning with the third wing and fourth wing; in this way, during the folding step of the pad, said third wing 102 and fourth wing 102 will match perfectly with said folded first wing and second wing 101 laid on the plane 100 of the pad.

More in particular, without prejudice to all that has been described so far, the solutions could be as follows:

In one case there may be blocks 30 (also called shoes 30) applied to the rollers and provided with suction nozzles, with said blocks 30 being translatable transversely on the surface of the roller 200 in such a way as to be able to move on the circumference of the roller from the periphery towards the center and vice versa (See schematization of FIG. 6—axial motion direction C-C). Such shoes 3 may be arranged on the roller 200 to trace a segment of chord 41 of the roller 200 (see FIG. 7).

In particular, the schematization of FIG. 6 shows the two blocks 30 provided with suction nozzles to generate a suction force and thus block said third wing 102 and fourth wing 102. In this way, the suction would act on the wings 102 hence gripping them and the translation of the blocks 30 (see arrow direction) would lead to a translation of the wings 102 by an amount necessary to perfectly superimpose them on the relative first wing 101 and second wing 101. In essence, the blocks 30 could translate along the axis C-C for example moving towards the center, thus bringing the two wings 102 (third wing 102 and fourth wing 102) to be drawn close to each other and thus compensating for the reduction in width of the wings 101 (first wing 101 and second wing 101) due to their folding at 180°, thus leading to a perfect overlap between them.

The translation motion in one direction and then in the opposite direction for the return to the initial position can be obtained in various ways.

For example, in one solution, it would be obtainable via a simple cam system per se widely known in the art. The cams would determine the reciprocal motion (in one direction and therefore also in the opposite direction) as a function of the rotation of the roller. As the roller rotates, a part of the block comes into contact with a cam profile that causes a motion in one direction and as the rotation continues, the cam profile is such as to then determine the motion in the opposite direction to then disengage from the block until the next turn is resumed and so on.

In a variant, the conformation itself of the roller may provide for buckling and/or depressions at specific points that cause the product above arranged to assume a shape such that the wings 101 are then in a position of perfect overlap with the wings 102 when the product is overturned on itself in wrapped over manner.

More specifically, a suction makes the product adhere well and buckling and/or depressions determine collection points that modify the width of the product such that the third wing and the fourth wing will be in line with the first wing and the second wing.

As said the first quick connection means and the second complementary quick connection means may be in the form of Velcro® such that the first quick connection means (e.g. the hooks) may for example be placed on the first wing 101 and second wing 101 to releasably couple with the second complementary quick connection means (e.g. the fibers) placed on the opposed third wing 102 and fourth wing 102.

Nothing precludes the use of quick means other than Velcro® as an adhesive material.

The invention claimed is:

1. An apparatus for folding a semifinished product of an absorbent product for sanitary use to form a product shaped as pants, the apparatus comprising:

a path of forward motion for the semifinished product, the path of forward motion comprising transversal folding devices configured to fold the semifinished product about a transverse line with respect to the path of forward motion so as to fold the semifinished product into two parts overlapping each other to form the product shaped as pants, and the semifinished product having wings comprising a first wing emerging from a flank of the semifinished product, a second wing opposite the first wing and emerging from an opposite flank of the semifinished product, a third wing, and a fourth wing; and folding means of the wings disposed upstream of the transversal folding devices and configured to overturn, and maintain in a laid position on a surface of the semifinished product, the first wing and the second wing until completion of formation of the product shaped as pants, wherein the folding means comprise one or more nozzles for providing one or more air jets and one or more fingers movable along the path of forward motion to overturn, and maintain, the wins in the laid position.

2. The apparatus according to claim 1, wherein the folding means are configured to fold the first wing and the second wing by 180° or about 180° and keep the first wing and the second wing in a folded position.

3. The apparatus according to claim 1, wherein the folding means are positioned along the path of forward motion.

4. The apparatus according to claim 1, wherein the one or more nozzles for providing the one or more air jets are positioned along the path of forward motion and are adapted to fold one of the wings of the semifinished product by lifting the one of the wings with respect to the surface of the semifinished product by an angle of 90° or about 90°.

5. The apparatus according to claim 4, further comprising at least two side shoes connected to edges of the path of forward motion, one of the at least two side shoes being arranged on a flank of the path of forward motion and another one of the at least two side shoes being arranged on an opposite flank of the path of forward motion so as to intercept the first wing and the second wing, the at least two side shoes being equipped with holes for a passage of the one or more air jets provided by the one or more nozzles.

6. The apparatus according to claim 5, wherein the path of forward motion is formed by at least one rotatable wheel, and wherein the at least two side shoes are disposed on board the at least one rotatable wheel.

7. The apparatus according to claim 6, wherein the at least two side shoes have a flat geometry, which traces a segment of a chord of the at least one of the at least one rotatable wheel where they are disposed, or alternatively, the at least two side shoes have a circular geometry configured to follow an arc of a circumference of the at least one of the at least one rotatable wheel.

8. The apparatus according to claim 5, wherein the folding means comprise, in combination with the one or more nozzles, overturning and maintaining devices integrated on board the path of forward motion and configured to completely overturn the one of the wings to lay the one of the wings on the surface of the semifinished product and maintaining the one of the wings in the laid position.

9. The apparatus according to claim 8, wherein the overturning and maintaining devices comprise the one or more fingers configured to overturn the one of the wings at least on the surface of the semifinished product, the one or more fingers being positioned along the path of forward motion.

10. The apparatus according to claim 9, wherein the one or more fingers are movable and configured to perform axial pushing movements such that, in use, the one or more fingers act on the one of the wings to overturn the one of the wings from a lifted position at 90° to a position laid on the surface, thus completing a rotation of 180° of the one of the wings.

11. The apparatus according to claim 9, wherein the path of forward motion comprises one or more areas provided with suction to maintain the wings in an overturned position on the surface at least until activation of the transversal folding devices ends to complete the product shaped as pants.

12. The apparatus according to claim 9, wherein the one or more fingers remain in a position intercepting the path of forward motion for maintaining the wings in an overturned position on the surface at least until activation of the transversal folding devices ends.

13. The apparatus according to claim 9, wherein the one or more fingers are shaped to not fully cover the wings on which the one or more fingers act, so as not to interfere with a coupling of the wings.

14. The apparatus according to claim 1, further comprising shoes arranged on opposite sides of the folding devices of the wings with respect to a longitudinal length of the semifinished product, the shoes being arranged to narrow a portion of the semifinished product longitudinally opposite to the first wing and the second wing.

15. The apparatus according to claim 14, wherein the shoes comprise openings through which a suction is applied on the semifinished product, the shoes being movable so as to cause the suction to drag the portion of the semifinished product, thus causing a transversal narrowing thereof.

16. The apparatus according to claim 1, further comprising lateral compression wheels for pressing the semifinished product when the semifinished product has been closed to form the product shaped as pants through the transversal folding devices.

* * * * *